Figure 1:
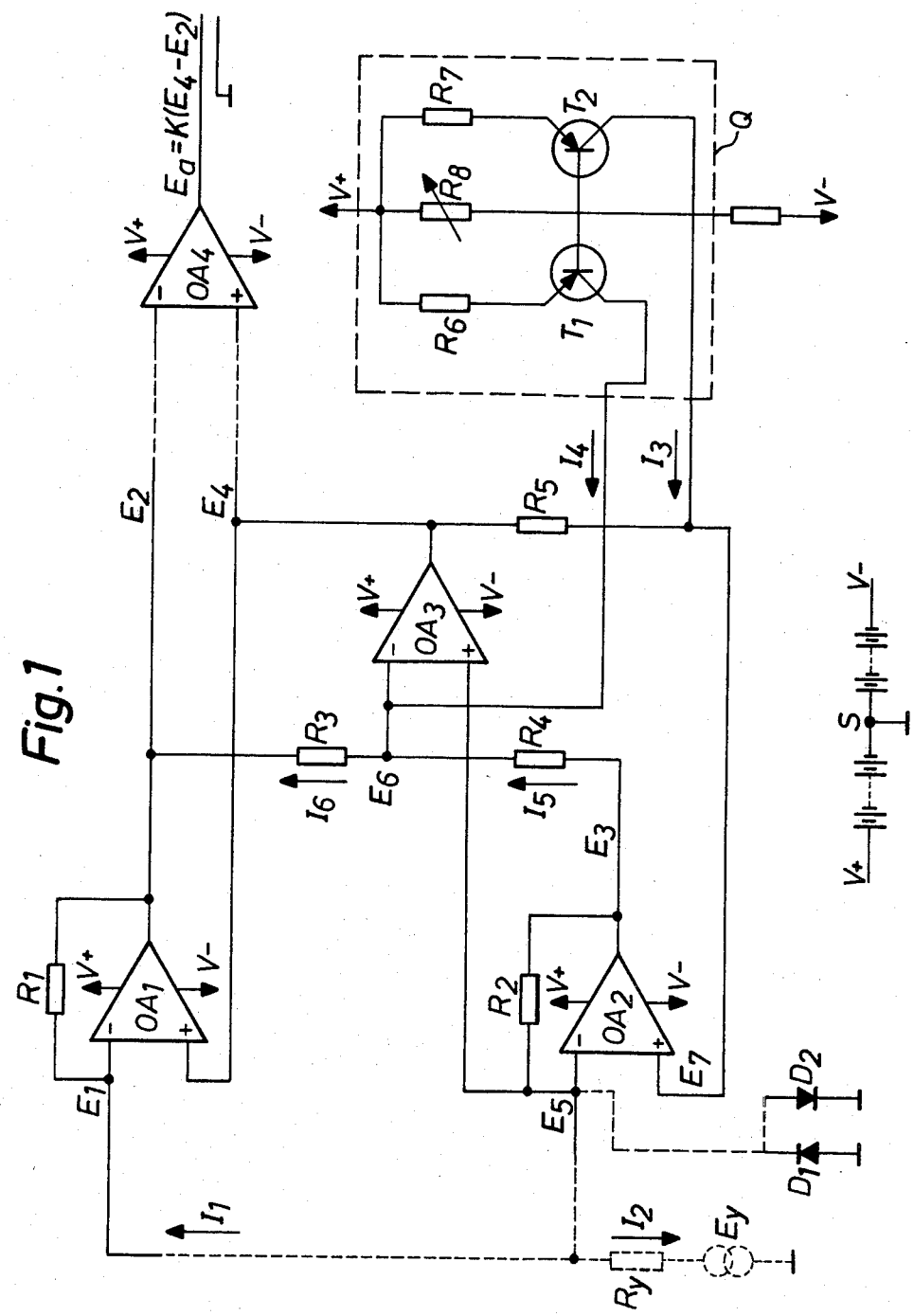

United States Patent

Fredericks

[11] 4,318,041
[45] Mar. 2, 1982

[54] CIRCUIT ARRANGEMENT FOR AN ELECTRO-CHEMICAL MEASURING DEVICE

[75] Inventor: George E. Fredericks, Graz, Austria
[73] Assignee: AVL AG, Schaffhausen, Switzerland
[21] Appl. No.: 64,266
[22] Filed: Aug. 6, 1979

[30] Foreign Application Priority Data

Aug. 21, 1978 [AT] Austria ................ 6084/78

[51] Int. Cl.³ .......................................... G01N 27/00
[52] U.S. Cl. ................... 324/71 R; 324/443; 324/450
[58] Field of Search ............. 324/71 R, 71 CP, 425, 324/438, 439, 444, 446, 449, 450

[56] References Cited

U.S. PATENT DOCUMENTS

| | | | |
|---|---|---|---|
| 3,441,490 | 4/1969 | Johansson | 324/439 |
| 3,722,276 | 3/1973 | Chandler | 324/443 |
| 3,742,348 | 6/1973 | Golibersuch | 324/71 CP |
| 3,852,666 | 12/1974 | Galwiler | 324/71 CP |
| 4,228,400 | 10/1980 | Bruckenstein | 324/450 |

*Primary Examiner*—Michael J. Tokar
*Attorney, Agent, or Firm*—Ladas & Parry

[57] ABSTRACT

A measuring circuit for use with an active polarized electrode, a reference electrode and a diaphragm which separates the solution to be examined from the electrolyte in which the electrodes are immersed. The output signals from the polarized electrode and from the reference electrode are processed as follows. The respective electrode is connected to one of the inputs of a respective operational amplifier (OA1, OA2) which serve as current voltage converters. The outputs of these amplifiers are then connected to a third operational amplifier (OA3) which detects the prevailing current difference in the electrode currents and initiates a necessary correction.

6 Claims, 2 Drawing Figures

CIRCUIT ARRANGEMENT FOR AN ELECTRO-CHEMICAL MEASURING DEVICE

The present invention relates to a circuit arrangement for an electro-chemical measuring device having an active polarised electrode, a reference electrode and a diaphragm which separates the solution to be examined from the electrolyte in which the electrodes are immersed.

Circuit arrangements of this kind are already known. Some are simple current measuring apparatus with an additional means for obtaining a polarisation voltage with ground as the reference point. Such arrangements function perfectly as long as the diaphragm insulation resistance is very high. When this is not the case undesirable currents may flow through the diaphragm, because the solution to be examined has not necessarily the same potential as the electrolyte. Added thereto is the possibility of an electro-chemical potential at the interface between the solution and the electrolyte within the diaphragm leak. The undesirable currents may influence the polarisation current to be measured and may distort the measuring results. Methods exist already for suppressing such diaphragm leak currents. E.g. the solution to be examined may be well insulated from ground and all other possible current sumps. Unfortunately this measure can be performed only with difficulty in most cases; in particular when other electrode systems are located in the same solution. Another method resides in the insulation of the entire measuring chain from ground and other current sumps. A separate supply voltage is necessary for the measuring chain and leads to increased costs.

In a $pO_2$ electrode system, which illustrates an example of such a system, currents must be measured in the nano ampere region in order to attain the bases for the value to be measured. Moreover a stable polarisation voltage between the active electrode and the reference electrode must be maintained during the measurement. Under these difficult conditions the undesirable current which flows through a prevailing diaphragm leak must be excluded in such electrode systems, because if the insulation resistance of the diaphragm in an oxygen- ($pO_2$) electrode deteriorates in consequence of a leak in its diaphragm, measurement faults may occur in consequence of undefined potential differences between the electrodes of such an electrical system and the solution to be examined. These potential differences cause currents through the reference electrode and the diaphragm leak.

We have now discovered a circuit arrangement which can compensate automatically for all likely voltages in the leak loop and can thus prevent any undesirable leak current.

This is attained in the circuit arrangement of the stated kind according to the invention in that the respective electrode is connected to one of the inputs of a respective operational amplifier, that the outputs of these operational amplifiers are connected to a third operational amplifier which detects a difference possibly occurring between the two electrode currents and changes the level of the first-mentioned operational amplifier in such a manner that this difference remains at zero.

The invention is further illustrated with reference to the accompanying drawings, in which:

FIG. 1 shows diagrammatically one possible circuit arrangement; and

Figure 2:
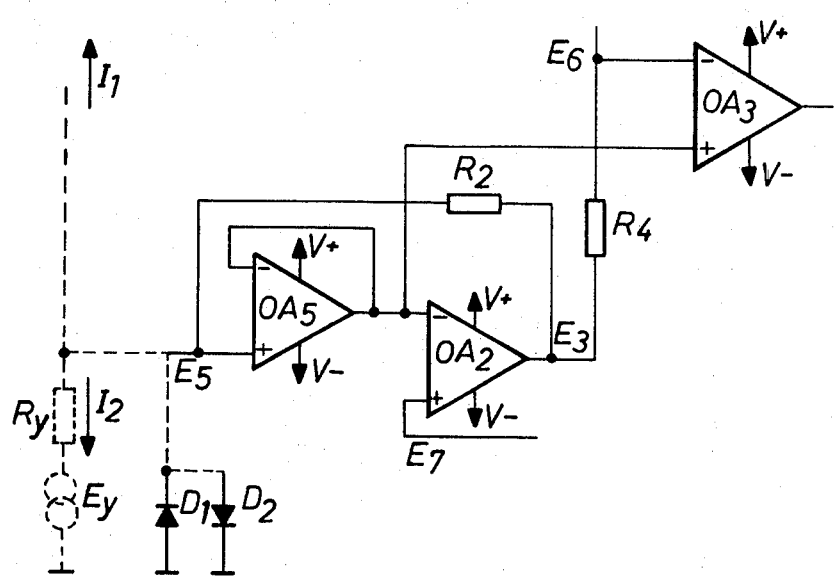

FIG. 2 shown a possible addition to this circuit arrangement.

A measuring device in which the present circuit arrangement can be employed, comprises one or more electrode systems which are of a kind known per se, so that the electrodes system need not be described here in detail. A polarized electrode, e.g. an oxygen electrode ($pO_2$) and a reference electrode are connected to respective inputs of the present circuit arrangement (FIG. 1). The polarized electrode is connected to a first operational amplifier OA1, this junction being denoted by E1. This operational amplifier OA1 is provided with feedback by means of a first resistor R1. The output E2 of this operational amplifier OA1 is fed to the inverting input of a further operational amplifier OA4 the non-inverting input of which is connected to the non-inverting input of the first operational amplifier OA1.

The object of this further operational amplifier OA4 is to convert the difference signal supplied to it to a single-pole output Ea. Therefore this operational amplifier OA4 measures only the magnitude of the difference between the signals at its inputs and is independent of the level of the whole circuit arrangement.

The reference electrode is connected to the inverting input of a second operational amplifier OA2, this junction being denoted by E5. This operational amplifier OA2 is likewise provided with feed-back by means of a resistor R2. The output E3 of this second operational amplifier OA2 is connected to the inverting input E6 of a third operational amplifier OA3 by way of a resistor R4. The input E6 of this third operational amplifier OA3 is then connected to the output E2 of the first operational amplifier OA1 by way of a resistor R3. The non-inverting input of the third operational amplifier OA3 is connected to the junction E5 at the input of the second operational amplifier OA2. The output E4 of the third operational amplifier OA3 is connected to the non-inverting input E4 of the first operational amplifier OA1 as well as also to the non-inverting input E7 of the second operational amplifier OA2, this last-mentioned connection being effected with the interposition of a resistor R5.

Since for the operation of the whole measuring system a polarisation voltage is necessary between the reference electrode and the polarised electrode, a double current source Q serving for this purpose is provided in the present circuit. This source Q comprises two transistors T1 and T2 which are fed by a feed source S. The feed source S may also serve as a feed source for the respective operational amplifier.

A voltage divider with a variable resistor R8 is connected between the connecting terminals V+ and V− of the double current source Q, the emitters of the transistors T1 and T2 being connected to a terminal of the feed source S by means of a respective resistor R6 and R7, respectively. The collector of the first transistor T1 is connected to the inverting input E6 of the third operational amplifier OA3. In contrast the collector of the second transistor T2 is connected to the non-inverting input of the second operational amplifier OA2. This source Q together with the resistors R3 and R5 produces the said polarisation voltage which, for a $pO_2$-system comprises a magnitude of approximately 700 mV and which is supplied to the electrodes on the paths described. The magnitude of this polarisation voltage which is produced by the currents I3 and I4 and the resistors R3 and R5 can be adjusted selectively by means of the variable resistor R8. The source Q ensures that the magnitude of the polarisation voltage, once adjusted, remains constant, namely independent of the magnitude of the current which flows out of the location E5 at the input of the second operational amplifier. Obviously other kinds of current sources may also be employed here; e.g. field effect current sources, if they possess the necessary stability over the working temperature range.

It is also advantageous to provide a voltage limiter which consists of diodes D1 and D2 connected in opposition. These voltage or potential limiters fix the upper and lower limit of the voltage or potential, respectively, which the circuit arrangement can assume during the operation thereof. When necessary, this potential range may be enlarged by a plurality of diodes in series connection or by a bias voltage in the cut-off direction for the diodes.

In FIG. 1, a prevailing leak in the diaphragm of an electrode system is illustrated by means of a series circuit which consists of a resistor Ry and a source Ey. One end of this series combination is connected to the reference electrode.

The circuit described has the property that it can measure a current I1 which flows between the points E5 and E1. If the analysed liquid—for example blood—does not contain oxygen, the current I1 is zero. As the concentration of oxygen increases, the magnitude of the current I1 increases also.

If the diaphragm has no leak, the resistence Ry is infinitely large. This has the consequence that no current I2 flows through the resistor Ry. Consequently the magnitude of the current I1 which flows out of E5 is equal to the magnitude of the current I1 which flows into the point E1 at the input of the first operational amplifier OA1. This may also be stated thus that the magnitude of the current at the points E1 and E5 is the same. Thus the current flows from the terminal V+ at the operational amplifier OA2 through the latter, through the feed-back resistor R2, through the point E5, through the reference electrode, the polarised electrode, the point E1, the resistor R1, the operational amplifier OA1 to the terminal V− at the first operational amplifier.

If the diaphragm comprises a leak, a leak current I2 flows therethrough which is added to the current I1 flowing out of the point E5. In such a case the magnitude of the currents in the point E1 and E5 is no longer equal. This inequality produces a difference voltage at the inputs of the third operational amplifier OA3. A highly amplified correction signal appears at the output of the third operational amplifier OA3 and is supplied to the non-inverting inputs of the first and second operational amplifier OA1 and OA2. This has the effect that the potential of the whole circuit is so adjusted that taking the voltage Ey into account, a leak current is prevented. This may alternatively be stated in this way. A difference in the electrode currents can occur only if a leak current I2 flows. A leak current I2 is possible only when the sum of all voltages in the leak loop is not equal to zero. The third operational amplifier OA3 ensures that the potential level of the electrolyte is so adjusted that the sum of all voltages in the leak loop is equal to zero. The adjustable double current source Q together with the two resistors R3 and R5 produces between the two electrodes an adjustable voltage difference, a polarisation voltage.

It is known from experience that the voltage Ey lies in most cases within the range of from 0 to 100 mV. However, the range of the level difference which such a circuit arrangement can assume during its operation, is very much greater for a diaphragm without leak. In such a case the respective potential level might have very different values. The conductance voltages of the diodes D1 and D2 set the limits for those of the potential level of the circuit arrangement; in this case the level may move within a voltage difference at approximately 1 V. Even if a leak is present in the diaphragm, the voltage Ey, as stated, reaches practically at most 100 mV, this lying with certainty within the limits fixed by the diodes D1 and D2. When necessary, this potential range may nevertheless be enlarged by connecting a plurality of diodes in series or by a bias voltage in the cut-off direction for the diodes.

Such a circuit arrangement ensures that the prevailing leak currents through the diaphragm are suppressed. Therefore it permits the measurement of the polarisation current proper of the active electrode, as well as the adjustment and maintenance of the respective required polarisation voltage. The life of the diaphragm can be extended, because reliable measuring results are obtained, until the diaphragm becomes so bad that a considerable quantity of the solution flows through the leak. However, this state of affairs is easily recognisable, because then instability and drifting occur during the calibration of the electrodes. When the present circuit arrangement is employed, the periodic examination of the diaphragm insulation resistance necessary heretofore is no longer necessary.

The manner of working of the electronic circuit arrangement described can be clarified further with reference to the following calculations.

As stated, I1 is the current which is to be evaluated and which is produced by the polarisation voltage between E5 and E1 dependently upon the ion concentration in the measuring solution.

As stated, I2 is the undesirable current which is caused by the unknown voltage Ey and which flows through an unknown resistance Ry the value of which may lie practically between 0 and infinity.

The two output voltages E2 and E4 constitute a difference output and they feed the amplifier OA4 which possesses a difference input and a high equal beat suppression. The actual circuit of this amplifier is unimportant, because it must possess only the transfer function Ea=K (E4−E2), wherein K is a constant.

Taking into account the negative feed-back and the high idling amplifications of the operational amplifiers OA1, OA2 and OA3, the following equations may be written down:

$$E1 = E4 \quad (1)$$
$$E5 = E6 = E7 \quad (2)$$
$$I4 + I5 = I6 \quad (3)$$
$$E4 = E7 - I3R5 \quad (4)$$
$$E2 = E1 - I1R1 \quad (5)$$
$$E3 = E5 + R2(I1 + I2) \quad (6)$$
$$I5 = \frac{E3 - E6}{R4} \quad (7)$$
$$I6 = \frac{E6 - E2}{R3} \quad (8)$$

From (2) and (7), there is obtained:

$$I5 = \frac{E3 - E5}{R4}$$

If the equation (6) is substituted therein for E3, we obtain $$I5 = \frac{E5 + R2(I1 + I2) - E5}{R4} = \frac{R2(I1 + I2)}{R4} \quad (9)$$

From (1) and (5), there results:

$$E2 = E4 - I1R1$$

From (2) and (4), there is obtained:

$$E4 = E5 - I3R5, \text{ and}$$

thus there is obtained:

$$E2 = E5 - I3R5 - I1R1 \quad (10)$$

From (2) and (8), there is obtained:

$$I6 = \frac{E5 - E2}{R3}$$

If (10) is substituted therein for E2:

$$I6 = \frac{E5 - E5 + I3R5 + I1R1}{R3} = \frac{I3R5 + I1R1}{R3} \quad (11)$$

There results then from (3), (9) and (11):

$$I4 + \frac{R2(I1 + I2)}{R4} = \frac{I3R5 + I1R1}{R3}$$

This equation may be re-written as:

$$I1(R2R3 - R1R4) = I3R4R5 - I2R2R3 - I4R3R4$$

If then $R2R3 = R1R4$, I1 disappears and we have:

$$I2R2R3 = R4(I3R5 - I4R3)$$

If we then make $I3R5 = I4R3$, I2 must be equal to zero. The last assumption may be written as:

$$I3/I4 = R3/R5$$

For parallel current sources, there may be written in general:

$$I3/I4 = R6/R7$$

However, errors may arise owing to inequality or non-linearity of the two transistors. In spite of this, if an integrated pair of transistors is used and simultaneously it is assumed that $$I4 = I3$$

the circuit is very accurate and stable, since the two collector voltages remain always the same (see equation 2).

It has become clear thereby that under the conditions
R7 = R6
R3 = R5
R2R3 = R1R4 the circuit maintains the current I2 at 0, independently of the value of I1 and the voltage Ey. Obviously Ey must not lie outside the equal beat voltage ranges of the operational amplifiers.

We see from equations (1), (2) and (4) that the polarisation voltage $$E5 - E1 = I3R5$$

remains constant, independently of the other voltage and current values. This voltage may also be adjusted by the variable resistor R8 which controls I3 and I4.

We see from equations (1) and (5) that the difference output voltage $$E4 - E2 = I1R1$$

is proportional to the polarisation current I1, independently of the other variables.

When the diaphragm insulation resistance (Ry in the circuit) is very high, the voltage level of the circuit is undefined, since one control is absent. As stated, the highly resistive diodes D1 and D2 limit the voltage range and serve at the same time as input protections.

It has been assumed in these calculations that the three operational amplifiers OA1, OA2 and OA3 possess a very high input impedance; i.e. that the input currents are very small in relation to the currents to be measured. However, operational amplifiers with a very high input impedance are expensive. It is possible to obtain a more economical circuit arrangement with a further operational amplifier OA5 (FIG. 2). The reference electrode is connected to the non-inverting input of this operational amplifier OA5. The output of the same is connected to the inverting input of the second operational amplifier OA2 and also directly to its own inverting input. The other end of the resistor R2 is connected in this case to the non-inverting input of the operational amplifier OA5.

The operational amplifier OA5 has a very high input impedance and is employed as impedance converter (voltage follower). Because of the very low output impedance the two operational amplifiers OA2 and OA3 are allowed to receive some current through their inputs. Thus two expensive operational amplifiers are substituted for by one expensive and two inexpensive ones. However the preceding calculations retain their validity, because even for this construction of the circuit arrangement the voltages at the input and at the output of the operational amplifier OA5 are always the same.

We claim:

1. A circuit arrangement for an electro-chemical measuring device having an active polarized electrode, a reference electrode and a diaphragm which separates a solution to be examined from an electrolyte in which the electrodes are to be immersed, which comprises:
   (i) first and second operational amplifiers which serve as current-voltage converters and each of which is provided with an inverting input and a non-inverting input;
   (ii) means connecting said electrodes respectively to the inverting inputs of said first and second operational amplifiers;
   (iii) a third operational amplifier provided with an inverting input and a non-inverting input;
   (iv) means connecting the non-inverting input of said third operational amplifier to the inverting input of said second operational amplifier;

(v) means connecting the output of said third operational amplifier to the non-inverting inputs of said first and second operational amplifiers; and (vi) a voltage divider connected across the outputs of said first and second operational amplifiers, said voltage divider comprising at least two serially-connected resistors having a common junction which is connected to the inverting input of said third operational amplifier, whereby said third operational amplifier determines the prevailing current difference in the electrode currents for initiating any necessary correction.

2. A circuit arrangement according to claim 1, in which the means connecting the reference electrode to the inverting input of said second operational amplifier includes an impedance converter.

3. A circuit arrangement as claimed in claim 1, which additionally comprises a double current source; the first output of which is connected to the inverting input of the third operational amplifier and the second output of which is connected to the non-inverting input of the second operational amplifier and to the output of the third operational amplifier through a resistor.

4. A circuit arrangement as claimed in claim 1, which additionally comprises a converter which converts the difference voltage delivered by the first and third operational amplifiers to a single-pole voltage.

5. A circuit arrangement as claimed in claim 1, in which the reference electrode is connected to ground.

6. A circuit arrangement as claimed in claim 1, in which the reference electrode is connected to a pre-selected blocking voltage by way of voltage limiters.

* * * * *